United States Patent [19]

Nardi et al.

[11] Patent Number: 4,705,797

[45] Date of Patent: Nov. 10, 1987

[54] N-(3,3-DIPHENYLPROPYL) AMINOETHYL ESTERS OF 1,4-DIHYDRO-2,6-DIMETHYL-PYRIDINE-3,5-DICARBOXYLIC ACID, COMPOSITIONS AND USE

[75] Inventors: Dante Nardi; Amedeo Leonardi, both of Milan; Gabriele Graziani, Arese; Giorgio Bianchi, Milan, all of Italy

[73] Assignee: Recordati S.A., Chemical and Pharmaceutical Company, Chiasso, Switzerland

[21] Appl. No.: 701,672

[22] Filed: Feb. 14, 1985

[30] Foreign Application Priority Data

Feb. 14, 1984 [GB] United Kingdom ................ 8403866

[51] Int. Cl.$^4$ ................ A61K 31/455; C07D 211/90; C07D 413/04
[52] U.S. Cl. ................ 514/356; 514/338; 546/271; 546/321
[58] Field of Search ................ 546/321, 271; 514/338, 514/356

[56] References Cited

U.S. PATENT DOCUMENTS 3,985,758 10/1976 Murakami et al. .................. 546/321
4,423,052 12/1983 Araki et al. .......................... 546/321
4,532,248 7/1985 Franckowiak et al. ............. 514/352

OTHER PUBLICATIONS

Burger, A. "Selected Pharmaceutical Testing Methods" vol. 8, Marcel Dekker, Inc., New York (1968) pp. 29–42.
Bossert, et al. "4-Aryldihydropyridines"Angew. Chem. Int. Ed. Engl. 20 (1981) pp. 762–769.
Schramm, et al, "Novel Dihydropyridines with Positive Inotropic Action" Nature, vol. 303 (Jun. 9, 1983) pp. 535–537.

*Primary Examiner*—Henry R. Jiles
*Assistant Examiner*—Dale A. Bjorkman
*Attorney, Agent, or Firm*—Burns, Doane, Swecker & Mathis

[57] ABSTRACT

Novel antihypertensive and coronary dilating asymmetric diesters of 1,4-dihydro-2,6-dimethyl-pyridine-3,5-dicarboxylic acid (or the stereoisomers or pharmaceutically acceptable acid addition salts thereof) have the general formula (I):

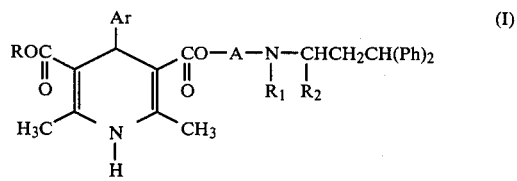

wherein Ph is phenyl, Ar is 2-nitrophenyl, 3-nitrophenyl, 2,3-dichlorophenyl or benzofurazan-4-yl, A is a straight or branched chain alkylene radical having from 2 to 6 carbon atoms, R is a straight or branched chain alkyl radical having from 1 to 6 carbon atoms, optionally mono-substituted by an alkoxy substituent having from 1 to 6 carbon atoms, $R_1$ is hydrogen, hydroxy or an alkyl radical having from 1 to 4 carbon atoms, and $R_2$ is hydrogen or methyl. The subject diesters are facilely prepared from the aldehydes ArCHO and esters of acetoacetic and 3-aminocrotonic acids.

8 Claims, No Drawings

N-(3,3-DIPHENYLPROPYL) AMINOETHYL ESTERS OF 1,4-DIHYDRO-2,6-DIMETHYL-PYRIDINE-3,5-DICARBOXYLIC ACID, COMPOSITIONS AND USE

BACKGROUND OF THE INVENTION

FIELD OF THE INVENTION

The present invention relates to novel asymmetric diesters of 1,4-dihydro-2,6-dimethyl-pyridine-3,5-dicarboxylic acid, to stereochemically isomeric forms and pharmaceutically acceptable acid addition salts thereof, to processes for the preparation of same and to pharmaceutical compositions comprised thereof.

SUMMARY OF THE INVENTION

A major object of the present invention is the provision of novel asymmetric diesters of 1,4-dihydro-2,6-dimethyl-pyridine-3,5-dicarboxylic acid, said diesters having the following general formula (I):

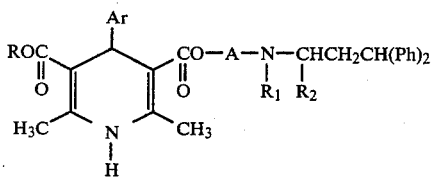
(I)

wherein Ph is phenyl, Ar is 2-nitrophenyl, 3-nitrophenyl, 2,3-dichlorophenyl or benzofurazan-4-yl, A is a straight or branched chain alkylene radical having from 2 to 6 carbon atoms, R is a straight or branched chain alkyl radical having from 1 to 6 carbon atoms, optionally mono-substituted by an alkoxy substituent having from 1 to 6 carbon atoms, $R_1$ is hydrogen, hydroxy or an alkyl radical having from 1 to 4 carbon atoms, and $R_2$ is hydrogen or methyl; as well as the pharmaceutically acceptable acid addition salts of such diesters.

Another object of the present invention is the provision of a process for the preparation of the esters of the general formula (I), said process comprising condensing a compound of the general formula (II):

Ar—CHO  (II)

wherein Ar is as defined above with a compound of the general formula (III):

  (III)

wherein $A_1$ is either (a) a radical of the general formula (IV):

  (IV)

wherein A, $R_1$, $R_2$ and Ph are as defined above, or (b) a radical of the general formula —AX wherein A is as defined above and X is a halogen atom, and then reacting the condensate thus formed with a compound of the general formula (V):

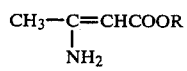  (V)

wherein R is as defined above, to give a compound of the general formula (VI):

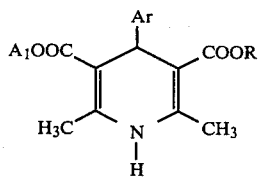  (VI)

wherein $A_1$, R and Ar are as defined above, and, if $A_1$ is the radical —AX as defined above, then converting —AX to a radical of the general formula (IV), also as defined above.

DETAILED DESCRIPTION OF THE INVENTION

More particularly according to the present invention, it will be appreciated that a variety of syntheses are encompassed within the metes and bounds of the process hereinbefore outlined. The reaction scheme to follow illustrates a number of same.

For example, the diesters (I) may be prepared by condensing a haloalkyl acetoacetate (IIIb) [III: $A_1$=—AX] with an aldehyde (II), reacting the condensate with an alkyl or alkoxyalkyl 3-aminocrotonate (V), and converting the radical —AX of the resultant 1,4-dihydropyridine derivative (VIb) [VI: $A_1$=—AX] to a radical (IV) by reaction with 3,3-diphenylpropylamine or a derivative thereof (VII). Alternatively, the radical (IV) may be introduced into the compound (III) prior to ring formation. This particular route begins with a compound (VIII):

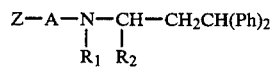  (VIII)

wherein Z is halogen or hydroxy and A, $R_1$, $R_2$ and Ph are as above defined. This is available from the amine (VII) by conventional alkylation to introduce haloalkyl or hydroxyalkyl group Z—A and reaction of the alkylated amine with diketene. Compound (IIIa) [III: $A_1$=IV] is condensed with an aldehyde (II) and the product is reacted with a 3-aminocrotonate (V).

Thus, said reaction scheme may be represented as:

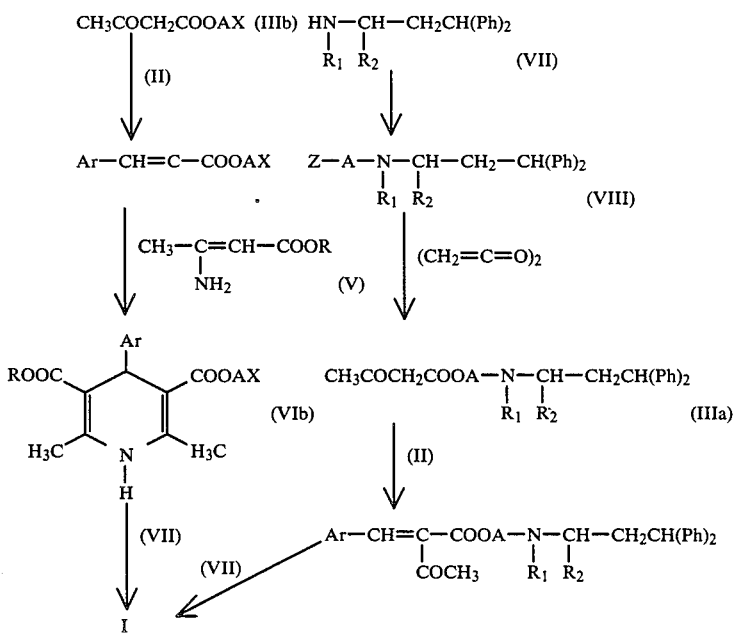

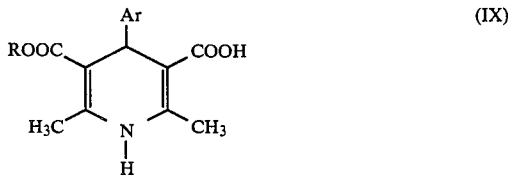

The above reaction scheme includes a synthesis of the pyridine ring. If a 1,4-dihydropyridine derivative (VIb) is already present, it is only necessary to condense it with an amine (VII). Similarly, if a free acid of the formula (IX):

$$\underset{\underset{H}{\overset{|}{N}}}{\overset{Ar}{\underset{H_3C}{\bigvee}}}\overset{COOH}{\underset{CH_3}{}}\quad (IX)$$

wherein R and Ar are as defined above is available, it is only necessary to condense it with a compound (VIII), or with a compound of the general formula YAX wherein Y is halogen and A and X are as above defined to give a 1,4-dihydropyridine derivative (VIb) for condensation with an amine (VII). These condensations are themselves within the ambit of the invention. When X is chlorine, they are preferably carried out in toluene or xylene under reflux, whereas when X is bromine they may be carried out in dimethylformamide at lower temperatures.

The diesters (I) obtained may be purified according to methods known per se, and crystallized as salts from suitable solvents in purified form. The pharmaceutically acceptable salts according to the invention may be prepared from the free bases in conventional manner. Preferred pharmaceutically acceptable acid addition salts are those of hydrochloric, sulfuric, maleic, succinic, citric, methanesulfonic and toluenesulfonic acids.

The diesters (I) and their salts according to the invention possess valuable antihypertensive activity and are also effective against coronary heart diseases. Accordingly, the invention also provides pharmaceutical compositions comprising diesters of the general formula (I) as above defined, or a pharmaceutically acceptable salt thereof in admixture with a pharmaceutically acceptable diluent or carrier.

The $LD_{50}$ of the compounds according to the invention was determined in the mouse, both i.p. and per os, according to the method described by C. S. Weil [Biometrics, 8, 249 (1952)].

The antihypertensive activity of the diesters according to the invention was evaluated in male hypertensive rats (SHR, Wister-Kyoto strain, 15–25 weeks old). The determination of blood pressure was performed by an indirect method [M. Gerald et al., Arzneim. Forsch., 18, 1825 (1968)]. The animals were prewarmed in a heating chamber at a temperature of from 35° C. to 37° C. for a period of 15 minutes before pressure determination. The compounds tested by oral route were dissolved or suspended in a 0.5% methylcellulose solution. Controls were given only the vehicle. Systolic blood pressure and heart rate were measured 1, 3, 5 and 7 hours after drug administration by means of a tail-cuff and a pulse transducer.

Coronary dilating activity was evaluated in anesthetized normotensive rats (weighing about 500 g), as the ability to antagonize methacholine induced coronary spasm. Rats were instrumented for methacholine infusion into the coronary ostium, while spastic activity was detected as ST segment elevation in $D_2$ ECG recording [K. Sakai et al., J. Pharm. Meth., 5, 325 (1981)].

The compounds tested by i.v. infusion were dissolved in water: dimethylformamide (9:1 by volume). Activity was detected as normalization of ECG tracing after compounds administration during methacholine infusion. The former test indicates that the diesters possess valuable antihypertensive activities; according to the methacholine test the compounds according to the invention are also considered effective against coronary heart diseases.

| Compound | $LD_{50}$ mg/kg | | $ED_{25}$ SHR | $ED_{50}$ |
|---|---|---|---|---|
| | i.p. | os | os mg/kg | iv µg/kg |
| 2279 | 121 | 279 | 7.3 | 297 |
| 2288 | 72 | 197 | 1.5 | 46 |
| 2263 | 171 | 254 | 3.4 | 197 |
| 2375 | 83 | 657 | 2.6 | 82 |

-continued

| Compound | LD$_{50}$ mg/kg i.p. | os | ED$_{25}$ SHR os mg/kg | ED$_{50}$ iv μg/kg |
|---|---|---|---|---|
| 2361 | 99 | 493 | 7.2 | — |
| 2350 | 50 | 116 | 3.0 | — |
| 2329 | 63 | 401 | 3.4 | — |
| 2352 | 222 | 2195 | 6.9 | — |
| 2383 | — | 500 | 3.4 | — |

ED$_{25}$ = antihypertensive activity
ED$_{50}$ = coronary dilating activity
— = not tested In order to further illustrate the present invention and the advantages thereof the following specific examples are given, it being understood that same are intended only as illustrative and in nowise limitative.

EXAMPLE 1

Preparation of 1-methyl-2-chloroethyl α-acetyl-3-nitrocinnamate

A solution containing 12.2 g of 3-nitrobenzaldehyde and 14.3 g of 1-methyl-2-chloroethyl acetoacetate in 80 ml of toluene, maintained at 0°–5° C., was saturated with hydrogen chloride gas. After two days at 20°–25° C., the residual hydrogen chloride was removed by bubbling nitrogen through the solution. The toluene was then evaporated off in vacuo. The residual oil was dissolved in dichloromethane and the solution thus obtained was washed with water until it was neutral. The organic phase which was separated and dried, was then evaporated to dryness under vacuum at 20° C. The residue was crystallized from 200 ml of isopropanol to give 20.70 g of the title compound, melting at 95°–96° C.

Following the procedure described above, but employing the appropriate aldehydes and acetoacetates, the following compounds were also prepared:

[i] 3-chloropropyl-α-acetyl-3-nitrocinnamate, m.p. 55°–60° C.;
[ii] 2-bromoethyl-α-acetyl-3-nitrocinnamate, m.p. 85°–95° C.;
[iii] 2-chloroethyl-α-acetyl-2,3-dichlorocinnamate, oil;
[iv] 1-methyl-2-chloroethyl α-acetyl-2,3-dichlorocinnamate, oil; and
[v] 2-chloroethyl-α-acetyl-β-(benzofurazan-4-yl)-acrylate, oil.

These compounds were mixtures of E/Z isomers and were employed as such in the further reactions, without separating the components.

EXAMPLE 2

Preparation of methyl 1-methyl-2-chloroethyl 1,4-dihydro-2,6-dimethyl-4-(3-nitrophenyl)-pyridine-3,5-dicarboxylate A solution comprising 18.72 g of 1-methyl-2-chloroethyl α-acetyl-3-nitrocinnamate, prepared as described in Example 1, and 7.12 g of methyl 3-aminocrotonate in 48 ml of isopropanol was refluxed under stirring for 210 minutes. After cooling, the reaction mixture was evaporated to dryness under vacuum and the oil thus obtained was chromatographed on silica gel (200 g) using chloroform as eluent. Evaporating the fractions containing a sole product (TLC, chloroform: ethylacetate 95:5) gave a thick oil, which was dissolved in diethyl ether. The solvent was then evaporated off at 20°–25° C. to give 15.75 g of the title compound, m.p. 95°–102° C., which could be employed without further purification.

Following the procedure described above, but using the appropriate 3-aminocrotonates and the α-acetyl cinnamates obtained as reported in Example 1, the following intermediates were obtained. They were all purified by column chromatography or by crystallization from suitable solvents:

[i] ethyl 2-chloroethyl 1,4-dihydro-2,6-dimethyl-4-(3-nitrophenyl)-pyridine-3,5-dicarboxylate, m.p. 158°–161° C.;
[ii] methyl 2-chloroethyl 1,4-dihydro-2,6-dimethyl-4-(2-nitrophenyl)-pyridine-3,5-dicarboxylate, m.p. 118°–120° C.;
[iii] isobutyl 2-chloroethyl 1,4-dihydro-2,6-dimethyl-4-(3-nitrophenyl)-pyridine-3,5-dicarboxylate, m.p. 146°–152° C.;
[iv] methyl 3-chloropropyl 1,4-dihydro-2,6-dimethyl-4-(3-nitrophenyl)-pyridine-3,5-dicarboxylate, m.p. 145°–146° C.;
[v] methyl 2-chloroethyl 1,4-dihydro-2,6-dimethyl-4-(2,3-dichlorophenyl)-pyridine-3,5-dicarboxylate, m.p. 167°–69° C.;
[vi] methyl 2-chloroethyl 1,4-dihydro-2,6-dimethyl-4-(benzofurazan-4-yl)-pyridine-3,5-dicarboxylate, m.p. 117°–118° C.;
[vii] isobutyl 1-methyl-2-chloroethyl 1,4-dihydro-2,6-dimethyl-4-(2,3-dichlorophenyl)-pyridine-3,5-dicarboxylate, low-melting solid;
[viii] 2-propoxyethyl 2-chloroethyl 1,4-dihydro-2,6-dimethyl-4-(3-nitrophenyl)-pyridine-3,5-dicarboxylate, m.p. 104°–106° C.; and
[ix] methyl 2-bromoethyl 1,4-dihydro-2,6-dimethyl-4-(3-nitrophenyl)-pyridine-3,5-dicarboxylate, m.p. 141–143° C.

EXAMPLE 3

Preparation of methyl 4-bromobutyl 1,4-dihydro-2,6-dimethyl-4-(3-nitrophenyl)-pyridine-3,5-dicarboxylate A suspension comprising 9.96 g of 1,4-dihydro-2,6-dimethyl-4-(3-nitrophenyl)-5-methoxycarbonyl-pyridine-3-carboxylic acid, 5.4 ml of 1,4-dibromobutane and 2.07 g of potassium carbonate in 60 ml of dimethylformamide was heated at 50° C. under stirring for 2.5 hours. The mixture was then cooled to room temperature, poured into 400 ml of water and extracted with diethyl ether. The ethereal extracts were then dried on anhydrous sodium sulfate and evaporated to dryness to give an oil which was purified by flash chromatography on silica gel columns, employing first chloroform and then chloroform: ethyl acetate 97:3 by volume as eluent.

The unitary TLC fractions (chloroform: ethyl acetate 9:1 by volume) were evaporated to give 11.75 g (84%) of the title compound, m.p. 113°–118° C.

EXAMPLE 4

Preparation of methyl N-(3,3-diphenyl-1-methylpropyl)-N-methyl-3-aminoethyl 1,4-dihydro-2,6-dimethyl-4-(3-nitrophenyl)-pyridine-3,5-dicarboxylate (compound 2202)

A solution of 3.94 g of methyl 2-chloroethyl 1,4-dihydro-2,6-dimethyl-4-(3-nitrophenyl)-pyridine-3,5-dicarboxylate and 4.78 g of 1,N-dimethyl-3,3-diphenylpropylamine in 12 ml of toluene was refluxed under stirring for 25 hours. Upon completion of the reaction the mixture was diluted with diethyl ether and the 1,N-dimethyl-3,3-diphenylpropylamine hydrochloride formed was collected by filtration. The filtrate was then evaporated, and the crude product thus obtained was purified by repeated chromatography on silica gel, using first chloroform, then chloroform: ethyl acetate (85:15 by volume) and lastly ethyl acetate as eluent. The purified product was dissolved in methanol and ethanolic hydrogen chloride was added. The solution was filtered and evaporated to dryness. Repeated washings with warm diethyl ether: acetone (98:2 by volume) afforded 2.98 g of the title compound, m.p. 113°–120° C.

Following the procedure described above, but using N-methyl-3,3-diphenylpropylamine instead of 1,N-dimethyl-3,3-diphenylpropylamine, methyl N-(3,3-diphenylpropyl)-N-methyl-2-aminoethyl 1,4-dihydro-2,6-dimethyl-4-(3-nitrophenyl)-pyridine-3,5-dicarboxylate (2206), m.p. 108°–113° C. was prepared.

The melting points of both compounds noted above refer to the respective hydrochlorides.

EXAMPLE 5

Preparation of methyl N-(3,3-diphenylpropyl)-2-aminoethyl 1,4-dihydro-2,6-dimethyl-4-(3-nitrophenyl)-pyridine-3,5-dicarboxylate (compound 2279)

A solution comprising 5.92 g of methyl 2-chloroethyl 1,4-dihydro-2,6-dimethyl-4-(3-nitrophenyl)- pyridine-3,5-dicarboxylate and 9.50 g of 3,3-diphenylpropylamine in 20 ml of xylene was refluxed under stirring for 105 minutes. The mixture was then cooled. By dilution with diethyl ether a semisolid compound was obtained, and it was separated from the liquid by decantation. The residue was treated with diethyl ether at 0°–4° C. and the supernatant was decanted. This procedure was repeated until a solid was obtained, and this was collected by filtration. Mother liquors and washings from the decantation were collected and evaporated to dryness under vacuum. The residue was chromatographed on a silica gel column (270 g) using a mixture of chloroform and acetone as eluent. Pure fractions were combined and the solvent was evaporated off. The residue was dissolved in diethyl ether and hydrogen chloride in diethyl ether was added. The solid (3.92 g) was crystallized from ethyl acetate or isopropyl acetate and recrystallized from ethyl acetate to give 3.46 g of the title compound, m.p. 128°–32° C.

Following the procedure described above, the following additional compounds were prepared:

[i] isobutyl N-(3,3-diphenylpropyl)-N-methyl-2-aminoethyl 1,4-dihydro-2,6-dimethyl-4-(3-nitrophenyl)-pyridine-3,5-dicarboxylate, m.p. 124°–129° C. (compound 2352);

[ii] methyl N-(3,3-diphenyl-1-methylpropyl)-N-methyl-3-aminopropyl 1,4-dihydro-2,6-dimethyl-4-(3-nitrophenyl)-pyridine-3,5-dicarboxylate, m.p. 113°–118° C. (compound 2244);

[iii] methyl N-(3,3-diphenylpropyl)-N-methyl-3-aminopropyl 1,4-dihydro-2,6-dimethyl-4-(3-nitrophenyl)-pyridine-3,5-dicarboxylate, m.p. 100°–107° C. (compound 2263);

[iv] ethyl N-(3,3-diphenylpropyl)-N-methyl-2-aminoethyl 1,4-dihydro-2,6-dimethyl-4-(3-nitrophenyl)-pyridine-3,5-dicarboxylate, m.p. 164°–167° C. (compound 2274);

[v] methyl 1, N-dimethyl-N-(3,3-diphenylpropyl)- 2-aminoethyl 1,4-dihydro-2,6-dimethyl-4-(3-nitrophenyl)-pyridine-3,5-dicarboxylate, m.p. 114°–123° C. (compound 2288);

[vi] methyl N-(3,3-diphenylpropyl)-N-methyl-2-aminoethyl 1,4-dihydro-2,6-dimethyl-4-(2,3-dichlorophenyl)-pyridine-3,5-dicarboxylate, m.p. 161° C. (compound 2306);

[vii] isobutyl N-(3,3-diphenylpropyl)-N-methyl-2-aminoethyl 1,4-dihydro-2,6-dimethyl-4-(3-nitrophenyl)-pyridine-3,5-dicarboxylate, m.p. 123°–124° C. (Compound 2329);

[viii] methyl N-(3,3-diphenylpropyl)-N-methyl-2-aminoethyl 1,4-dihydro-2,6-dimethyl-4-(benzofurazan-4-yl)-pyridine-3,5-dicarboxylate, m.p. 161°–166° C. (compound 2344);

[ix] isopropyl N-(3,3-diphenylpropyl)-N-methyl-2-aminoethyl 1,4-dihydro-2,6-dimethyl-4-(3-nitrophenyl)-pyridine-3,5-dicarboxylate, m.p. 160°–164° C. (compound 2350); and

[x] methyl N-(3,3-diphenylpropyl)-N-methyl-2-aminoethyl 1,4-dihydro-2,6-dimethyl-4-(2-nitrophenyl)-pyridine-3,5-dicarboxylate H2O, m.p. 118°14 125° C. (compound 2332).

All melting points of the compounds noted above refer to the respective hydrochlorides.

EXAMPLE 6

Preparation of methyl N-(3,3-diphenylpropyl)-N-methyl-4-aminobutyl 1,4-dihydro-2,6-dimethyl-4-(3-nitrophenyl)-pyridine-3,5-dicarboxylate (compound 2361)

A solution comprising 9.34 g of methyl 4-bromobutyl 1,4-dihydro-2,6-dimethyl-4-(3-nitrophenyl)-pyridine-3,5-dicarboxylate (prepared as described in Example 3) and 9.0 g of N-methyl-3,3-diphenylpropylamine in 15 ml of dimethylformamide was maintained for 16 hours at room temperature. The solution was then diluted with 250 ml of diethyl ether, and the starting amine hydrobromide thus formed was collected by filtration.

The filtered solution was washed twice with water and the organic solvent was removed under vacuum. The oily residue was then purified by flash chromatography on silica gel columns using chloroform: acetone (from 95:5 to 7:3 by volume) mixtures as eluent. By evaporating the unitary TLC fractions (chloroform: diethyl ether 1:1 by volume) under vacuum, an oil was obtained. The oil was dissolved in methanol and the solution was acidified with hydrogen chloride in ethanol and evaporated under vacuum to give an oily residue. This was dissolved in acetone, and the solution was again evaporated in vacuo.

The solid residue thus obtained was dissolved in 300 ml of methyl acetate and the solution filtered and slowly diluted with 900 ml of diethyl ether, maintaining in the mixture a methyl acetate: diethyl ether ratio of 1:3 by volume. The mixture was then stirred at 0° C. to give a precipitate which was collected by filtration and purified.

7.0 g of the hydrochloride hemihydrate of the title compound, m.p. 91°–103° C., were obtained.

EXAMPLE 7

Preparation of methyl N-(3,3-diphenylpropyl)-N-hydroxy-2-aminoethyl 1,4-dihydro-2,6-dimethyl-4-(3-nitrophenyl)-pyridine-3,5-dicarboxylate (compound 2410)

3 ml of triethylamine were added to a solution of 2.40 g of N-hydroxy-3,3-diphenylpropylamine in 17 ml of dimethylformamide. 4.39 g of methyl 2-bromoethyl 1,4-dihydro-2,6-dimethyl-4-(3-nitrophenyl)-pyridine-3,5-dicarboxylate were added to the mixture. The mixture was then maintained in a nitrogen atmosphere and heated for 160 minutes at 105° C. After cooling, the mixture was poured into water and extracted with a diethyl ether: ethyl acetate mixture. The organic layer was washed many times with water and then dried. The solvent was evaporated off in vacuo. The oily residue obtained was purified first by chromatography on a silica gel column with ethyl acetate gradient in toluene and then on a silica gel column containing ammonia at 5.5% by weight with about 6 N methanolic ammonia gradient in chloroform. The solid thus obtained was dissolved in a 2:1 by volume acetone: diethyl ether mixture and hydrogen chloride in diethyl ether was added. The hydrochloride hemihydrate of the title compound was filtered off, washed with isopropanol and dried at 100° C. and 0.5 mmHg for 1 hour. Yield 1.51 g, m.p. 100°–105° C.

EXAMPLE 8

Preparation of methyl 1,N-dimethyl-N-(3,3-diphenylpropyl)-3-aminopropyl 1,4-dihydro-2,6-dimethyl-4-(3-nitrophenyl)-pyridine-3,5-dicarboxylate (compound 2366)

A solution of 3.72 ml of 3-oxo-but-1-ene was added dropwise, over a period of 20 minutes and such that the temperature did not exceed 2°–3° C., to a cooled solution of 7.87 g of N-methyl-3,3-diphenylpropylamine in 7 ml of diethyl ether. The solution thus obtained was evaporated in vacuo at room temperature to give 10.3 g of N-methyl-N-(3,3-diphenylpropyl)-4-aminobutan-2-one (100%) as free base, shown to be practically pure by TLC (chloroform: methanol 9:1 by volume) which could be used as such for further reactions. This compound could be transformed into the corresponding hydrochloride (m.p. 133°–135° C.) by treating the free base with hydrogen chloride in diethyl ether, and crystallizing the product thus obtained first from acetone: ethyl acetate: isopropanol then from acetone.

To a solution of 9.16 g of the compound obtained as described above in 30 ml of methanol and maintained at 0° C., within 5 minutes 0.90 g of sodium borohydride were slowly added. When the addition was completed, the methanol was evaporated off in vacuo and the residue treated with water (about 100 ml) and diethyl ether (about 100 ml). The water was then washed with diethyl ether and the ethereal phases were combined, dried on anhydrous sulfate and evaporated to dryness in vacuo. The product (9.25 g) thus obtained, N-methyl-N-(3,3-diphenylpropyl)-4-aminobutan-2-ol, was a reddish oil unitary at TLC (chloroform: methanol 9:1 by volume).

A suspension comprising 7.44 g of the product from the last step, 12.46 g of 1,4-dihydro-2,6-dimethyl-4-(3-nitrophenyl)-5-methoxycarbonyl-pyridine-3-carboxylic acid, 8.51 g of N,N'-dicyclohexylcarbodiimide and 0.54 g of 4-dimethylaminopyridine in 50 ml of dimethylformamide was stirred at room temperature for 8 days. The suspension was then diluted with 450 ml of diethyl ether and the N,N'-dicyclohexylurea thus precipitated was collected by filtration. The filtered solution was washed with water (3×200 ml). The organic phase was dried and then evaporated off in vacuo. The oil thus obtained was purified by flash chromatography on silica gel columns using chloroform: ethyl acetate mixtures (1:1 by volume) as eluent. The fractions which were unitary at TLC (ethyl acetate) were evaporated to give a semisolid residue. This residue was dissolved in diethyl ether and the solution thus obtained was filtered and acidified with hydrogen chloride in diethyl ether to give a solid which was collected by filtration. The solution of this solid in 200 ml of ethyl acetate was diluted with 600 ml of ether, maintaining acetate: diethyl ether ratio of 1:3 by volume. The mixture was stirred at 0° C. until a precipitate was obtained. The operation was repeated three times, to give 8.50 g of the hydrochloride of the title compound, m.p. 93°–110° C.

EXAMPLE 9

Preparation of 2,N-dimethyl-N-(3,3-diphenylpropyl)-1-amino-2-propanol

A mixture of 16.87 g of N-methyl-3,3-diphenylpropylamine and 3.1 ml of 1-chloro-2-methyl-2-propanol in 20 ml of xylene was refluxed under stirring for 8 hours. After cooling at 15°–20° C., the suspension was diluted with diethyl ether and the starting amine hydrochloride thus obtained was collected by filtration. The solvent was removed from the filtrate in vacuo to give an oil which was then purified by flash chromatography on silica gel columns, employing chloroform with increasing amounts of methanol as eluent. The unitary TLC fractions (chloroform: methanol 94:6 by volume) were evaporated to give 7.8 g of the title compound as a brown oil.

EXAMPLE 10

Preparation of N-methyl-N-(3,3-diphenylpropyl)-1-amino-2-propanol 6.38 g of 1,2-epoxypropane was added to a solution of 22.5 g of N-methyl-3,3-diphenylpropylamine in 60 ml of methanol. The solution was maintained at 15°–20° C. for 3 days, and then an additional 1.16 g of 1,2-epoxypropane was added. This solution was maintained for 24 hours at room temperature. The methanol was evaporated off and the product purified by chromatography on a silica gel column (methanol gradient in chloroform), to give 24 g of the title compound as colorless oil.

EXAMPLE 11

Preparation of 1,1,N-trimethyl-N-(3,3-diphenylpropyl)-2-aminoethyl acetoacetate

A solution of 13.10 g of the compound as prepared in Example 9 in 10 ml of toluene was heated to 85° C. 3.6 ml of diketene were added dropwise over a period of 10 minutes, maintaining the temperature below 100° C. The solution was then heated for 2 hours at 80° C. After cooling at 15°–20° C. the mixture was evaporated in vacuo and the oily residue was purified by flash chromatography on silica gel columns using chloroform containing increasing amounts of methanol as eluent. The unitary TLC fractions (chloroform: methanol 95:5 by volume) were evaporated to dryness to give 12.3 g of the title compound as a brown oil.

EXAMPLE 12

Preparation of 1,N-dimethyl-N-(3,3-diphenylpropyl)-2-aminoethyl acetoacetate

Following the procedure described in Example 11, but using the compound prepared in Example 10 instead of that prepared in Example 9, the title compound was obtained as an oil.

EXAMPLE 13

Preparation of 1,1,N-trimethyl-N-(3,3-diphenylpropyl)-2-aminoethyl α-acetyl-3-nitrocinnamate Hydrogen chloride was bubbled into a solution of 3.78 g of 3-nitrobenzaldehyde and 9.54 g of the compound prepared in Example 11 in 25 ml of chloroform, cooled at 0° C., until the solution was saturated. The solution was maintained for 3 days at 15° C. It was then diluted with chloroform and washed with dilute aqueous sodium hydroxide solution until neutral. The organic phase was dried and the solvent was evaporated off. The solid thus obtained was dissolved in ethyl acetate and the solution was cooled at 0° C. A slight excess of hydrogen chloride in diethyl ether was added. The solid thus formed was repeatedly treated with diethyl ether to give 12.50 g of the title compound, m.p. 65°-80° C. The product was an E/Z isomeric mixture, and was used as such in further reactions.

EXAMPLE 14

Preparation of 1,N-dimethyl-N-(3,3-diphenylpropyl)-2-aminoethyl α-acetyl-3-nitrocinnamate Following the procedure described in Example 13, but using the compound prepared in Example 12 instead of that prepared in Example 11, the title compound was obtained as an oil. The product was an E/Z isomeric mixture, and was used as such in further reactions.

EXAMPLE 15

Preparation of 1,N-dimethyl-N-(3,3-diphenylpropyl)-2-aminoethyl α-acetyl-2,3-dichlorocinnamate Following the procedure described in Example 14, but using 2,3-dichlorobenzaldehyde instead of 3-nitrobenzaldehyde, the title compound was obtained as an oil. The product was an E/Z isomeric mixture, and was used as such in further reactions.

EXAMPLE 16

Preparation of methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate (compound 2375)

A solution of 2.37 g of methyl 3-aminocrotonate and 10.29 g of the compound prepared in Example 13 in 15 ml of isopropanol was refluxed for 3 hours. The mixture was then cooled and evaporated to dryness in vacuo. The oily residue thus obtained was purified by flash chromatography on silica gel columns, using chloroform with increasing amounts of acetone as eluent. The unitary TLC fractions (chloroform: acetone, 9:1 by volume) were evaporated and the solid thus obtained was dissolved in methanol. A slight excess of ethanolic hydrogen chloride was added and the solution was evaporated to dryness. The residue was dissolved in acetone and again evaporated in vacuo. The residue was crystallized from 2 liters of water containing 2 ml of 1 N hydrochloric acid and 5 ml of water saturated with sodium chloride, to give 4.8 g of the hydrochloride hemihydrate of the title compound, m.p. 119°-123° C.

EXAMPLE 17

Preparation of isobutyl 1,N-dimethyl-N-(3,3-diphenylpropyl)-2-aminoethyl 1,4-dihydro-2,6-dimethyl-4-(2,3-dichlorophenyl)-pyridine-3,5-dicarboxylate (compound 2383)

Following the procedure described in Example 16, but using isobutyl 3-aminocrotonate instead of methyl 3-aminocrotonate and the compound of Example 15 instead of that of Example 13, the hydrochloride of the title compound, m.p. 162°-164° C., was obtained.

EXAMPLE 18

Preparation of 2-propoxyethyl 1,N-dimethyl-N-(3,3-diphenylpropyl)-2-aminoethyl 1,4-dihydro-2,6-dimethyl-4-(2,3-dichlorophenyl)-pyridine-3,5-dicarboxylate (compound 2400)

Following the procedure described in Example 17, but using 2-propoxyethyl 3-aminocrotonate instead of isobutyl 3-aminocrotonate, the hydrochloride hydrate of the title compound, m.p. 108°-118° C., was obtained.

EXAMPLE 19

Preparation of 2-propoxyethyl 1,N-dimethyl-N-(3,3-diphenylpropyl)-2-aminoethyl 1,4-dihydro-2,6-dimethyl-4-(3-nitrophenyl)-pyridine-3,5-dicarboxylate (compound 2408)

Following the procedure described in Example 18, but using the compound of Example 14 instead of that of Example 15, the hydrochloride hemihydrate of the title compound, m.p. 85°-92° C., was obtained.

EXAMPLE 20

Preparation of 2-propoxy-1,1-dimethylethyl 1,N-dimethyl-N-(3,3-diphenylpropyl)-2-aminoethyl 1,4-dihydro-2,6-dimethyl-4-(3-nitrophenyl)-pyridine-3,5-dicarboxylate (compound 2409)

Following the procedure described in Example 19, but using 2-propoxy-1,1-dimethylethyl 3-aminocrotonate instead of 2-propoxyethyl 3-aminocrotonate, the hydrochloride hemihydrate of the title compound, m.p. 86°-95° C., was obtained.

EXAMPLE 21

Preparation of 2-propoxyethyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate (compound 2411)

Following the procedure described in Example 16, but using 2-propoxyethyl 3-aminocrotonate instead of methyl 3-aminocrotonate, the hydrochloride hemihydrate of the title compound, m.p. 87°-92° C., was obtained.

EXAMPLE 22

Preparation of 2-propoxy-1,1-dimethylethyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate (compound 2412)

Following the procedure described in Example 16, but using 2-propoxy-1,1-dimethylethyl 3-aminocrotonate instead of methyl 3-aminocrotonate, the hydrochloride hemihydrate of the title compound, m.p. 88°-92° C., was obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

We claim:

1. Methyl N-(3,3-diphenylpropyl)-N-methyl-2-aminoethyl 1,4-dihydro-2,6-dimethyl-4-(benzofurazan-4-yl)-pyridine-3,5-dicarboxylate, or a stereoisomer or pharmaceutically acceptable acid addition salt thereof.

2. Methyl-N-(3,3-diphenylpropyl)-N-hydroxy-2-aminoethyl 1,4-dihydro-2,6-dimethyl-4-(3-nitrophenyl)-pyridine-3,5-dicarboxylate, or a stereoisomer or pharmaceutically acceptable acid addition salt thereof.

3. Methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate, or a stereoisomer or pharmaceutically acceptable acid addition salt thereof.

4. 2-Propoxy-1,1-dimethylethyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate, or a stereoisomer or pharmaceutically acceptable acid addition salt thereof.

5. A pharmaceutical composition of matter for use as an antihypertensive or as a coronary dilator comprising an antihypertensive or coronary dilating amount of a member selected from the group consisting of
- methyl N-(3,3-diphenylpropyl)-N-methyl-2-aminoethyl 1,4-dihydro-2,6-dimethyl-4-(benzofurazan-4-yl)-pyridine-3,5-dicarboxylate;
- methyl N-(3,3-diphenylpropyl)-N-hydroxy-2-aminoethyl 1,4-dihydro-2,6-dimethyl-4-(3-nitrophenyl)-pyridine-3,5-dicarboxylate;
- methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate; and
- 2-propoxy-1,1-dimethylethyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate;

or a stereoisomer or pharmaceutically acceptable acid addition salt thereof, and a pharmaceutically acceptable diluent or carrier therefor.

6. A pharmaceutical composition of matter for use as an antihypertensive or as a coronary dilator comprising an antihypertensive or coronary dilating amount of methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate or a stereoisomer or pharmaceutically acceptable acid addition salt thereof, and a pharmaceutically acceptable diluent or carrier therefor.

7. A method of eliciting an antihypertensive or coronary dilating response in a mammalian organism, comprising administering to a mammalian organism in need of such treatment a member selected from the group consisting of
- methyl N-(3,3-diphenylpropyl)-N-methyl-2-aminoethyl 1,4-dihydro-2,6-dimethyl-4-(benzofurazan-4-yl)-pyridine-3,5-dicarboxylate;
- methyl N-(3,3-diphenylpropyl)-N-hydroxy-2-aminoethyl 1,4-dihydro-2,6-dimethyl-4-(3-nitrophenyl)-pyridine-3,5-dicarboxylate;
- methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate; and
- 2-propoxy-1,1-dimethylethyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate;

or a stereoisomer or pharmaceutically acceptable acid addition salt thereof.

8. A method of eliciting an antihypertensive or coronary dilating response in a mammalian organism, comprising administering to a mammalian organism in need of such treatment
methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate; or a stereoisomer or pharmaceutically acceptable acid addition salt thereof.

* * * * *